Figure 1:
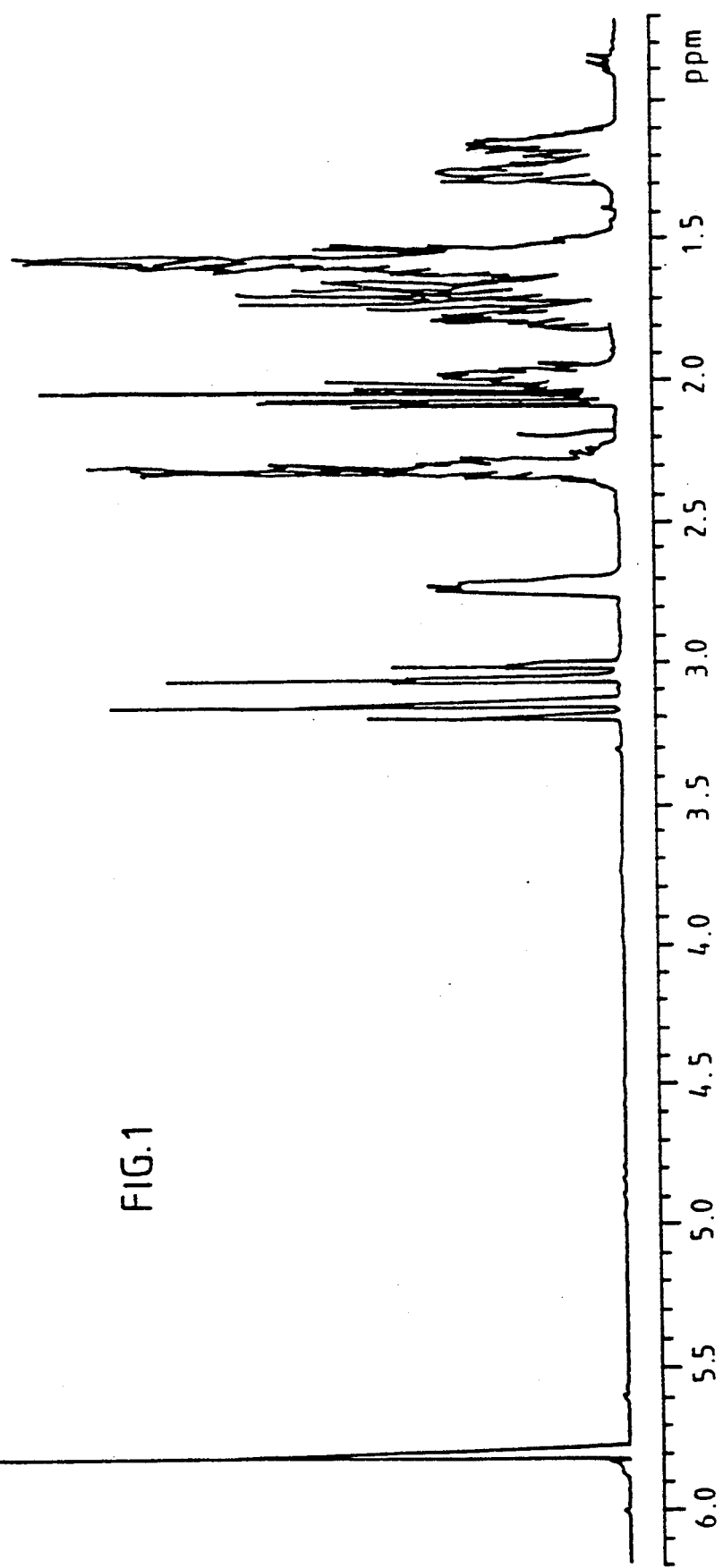

United States Patent [19]

Hopp et al.

[11] Patent Number: 5,212,153
[45] Date of Patent: May 18, 1993

[54] CYCLOPENTYL-CYANOMETHYL-CYCLO-PENTENES, PROCESS FOR THEIR PREPARATION AND THEIR USE AS ODORIFEROUS SUBSTANCES

[75] Inventors: Rudolf Hopp; Thomas Thielmann, both of Holzminden; Wilhelm Göttsch, Bevern, all of Fed. Rep. of Germany

[73] Assignee: Haarmann & Reimer GmbH, Holzminden, Fed. Rep. of Germany

[21] Appl. No.: 862,043

[22] Filed: Apr. 2, 1992

[30] Foreign Application Priority Data

Apr. 12, 1991 [DE] Fed. Rep. of Germany ........ 4111902

[51] Int. Cl.$^5$ .................... A61K 7/46; C07C 253/30; C07C 255/31
[52] U.S. Cl. ........................................ 512/6; 558/374; 558/432
[58] Field of Search .................... 558/432, 430; 512/6

[56] References Cited

U.S. PATENT DOCUMENTS

| 4,722,808 | 2/1988 | Kaufhold et al. | 512/6 |
| 4,755,615 | 7/1988 | Kaufhold et al. | 558/374 |
| 4,851,552 | 7/1989 | Kaufhold | 558/374 X |
| 4,912,088 | 3/1990 | Brunke et al. | 512/6 |
| 5,008,429 | 4/1991 | Kaufhold et al. | 558/374 |

FOREIGN PATENT DOCUMENTS

| 0016650 | 10/1980 | European Pat. Off. . |
| 0149054 | 7/1985 | European Pat. Off. . |
| 0302816 | 2/1989 | European Pat. Off. . |

*Primary Examiner*—Joseph Paul Brust
*Attorney, Agent, or Firm*—Sprung, Horn Kramer & Woods

[57] ABSTRACT

New nitriles which are odoriferous substances having an extremely fresh note are accessible by Knoevenagel condensation of 2-cyclopentyl-cyclopentanone and cyanoacetic acid and decarboxylation of the reaction product.

6 Claims, 2 Drawing Sheets

* Small residue of

CYCLOPENTYL-CYANOMETHYL-CYCLOPENTENES, PROCESS FOR THEIR PREPARATION AND THEIR USE AS ODORIFEROUS SUBSTANCES

The invention relates to new compounds of the formula

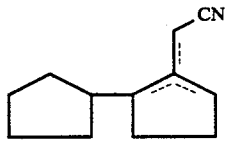
(I)

wherein the broken line indicates the three possible positions of a C=C double bond, to a process for the preparation of these compounds by Knoevenagel condensation of 2-cyclopentyl-cyclopentanone and cyanoacetic acid and decarboxylation of the reaction product, and to the use of the new compounds as odoriferous substances.

The Knoevenagel condensation can be carried out in a manner which is known per se (compare, for example, Organikum, 15th edition, VEB Deutscher Verlag der Wissenschaften, Berlin, 1984, page 571 et seq.). As a rule 1 to 3, preferably 1 to 2, mol of cyanoacetic acid are employed per mole of 2-cyclopentylcyclopentanone. The reaction is carried out in the presence of 0.005 to 0.5, preferably 0.05 to 0.3 mol of catalyst per mole of 2-cyclopentylcylcopentanone, if appropriate in the presence of 0.1 to 1, preferably 0.2 to 0.5, mol of glacial acetic acid, possible catalysts being, for example, piperidine, β-alanine or ammonium acetate. The reaction can thus best be carried out in an organic solvent which forms an azeotrope with water. Suitable organic solvents of this type include aromatics, such as benzene, toluene and xylene; these are in general employed in amounts of 100 to 1,000, preferably 100 to 500, ml per mole of 2-cyclopentylcyclopentanone. The reaction temperature is best chosen such that the primary product formed is decarboxylated immediately; the temperature is preferably 100° to 160°, in particular 135° to 145° C. As soon as the formation of water and carbon dioxide has ended, the reaction mixture can be worked up.

The 3 possible isomers are not all formed in the same amount:

The cyanomethylene a derivative of the formula (II)

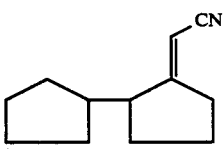
(II)

is formed in a minor amount and its smell is of no interest. The preferred cyclopentyl-cyclomethylcyclopentenes according to the invention correspond to the formula (III)

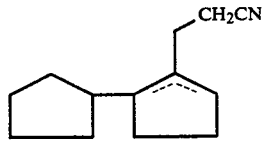
(III)

wherein the broken line indicates the two possible positions of a C=C double bond.

The two isomers of formulae (IV) and (V)

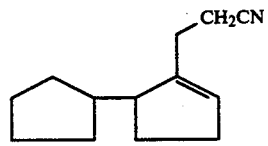
(IV)

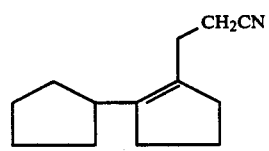
(V)

are also not equivalent, as the following descriptions of their smells show:

Compound IV: aldehydic, melon-like green;
Compound V: watery, extremely potent marine algae note, somewhat fruity, like gooseberries or rhubarb.

The ratio of the isomers formed can be influenced by the reaction conditions (compare Examples 1 and 2). Although the absence of glacial acetic acid and the use of relatively small amounts of solvent (Example 1) gives a higher overall yield, the yield of the desired product (V) is lower.

In the presence of a strong base such as an alkali metal alcoholate (for example sodium isopropylate), the less desirable isomer IV is already partly isomerised into the desired isomer V at room temperature (compare Example 3).

The compounds (I) according to the invention can be used in combination with other odoriferous substances which are known per se (Arctander, Perfume and Flavor Chemicals, Montclair, N.J. (USA), 1969) and essential oils which are known per se (Arctander, Perfume and Flavor Materials of Natural Origin, Elisabeth, N.J. (USA), 1960) and lead to perfume bases and odoriferous substance compositions which have highly expressive notes and are outstandingly suitable for perfuming finished products in the aerosol, detergent and domestic cleaner sector, and also the fine perfumery and cosmetics sector, for example for detergents, hair care agents, bath additives, dishwashing agents, washing powders, soaps, anti-perspirants, powders, creams, shaving lotion, aftershave lotions, air fresheners, WC cleaning agents and sunscreen agents.

The isomeric nitriles of the formula (I) can be employed here individually or as a mixture.

The compounds I according to the invention are in general employed in these preparations in an amount of 0.001 to 1% by weight, preferably 0.01 to 0.1% by weight, based on the finished perfume oil.

The perfume compositions and perfumed products can be prepared in the customary manner, for example by bringing the components together.

The percentage data in the following examples denote percentages by weight.

EXAMPLES

Example 1

304 g (2 mol) of 2-cyclopentylcyclopentanone, 205 g (2.4 mol) of cyanoacetic acid and 40 g (0.45 mol) of ammonium acetate in 300 g of xylene are heated under reflux, using a water separator, in a three-necked flask fitted with a stirrer, water separator and gas meter. After 6 hours, 67 g of an aqueous phase and about 60 l of $CO_2$ have been split off. The reaction mixture is washed successively with 100 g of 10% strength sulphuric acid, with 200 g of 5% strength sodium hydroxide solution and with water and is distilled over a 30 cm packed column. In addition to 80 g of 2-cyclopentyl-cyclopentanone (T(bottom)=130° C.; (T(head)=85° C.; 0.6 mbar), 180 g of the nitriles of the formula (I) according to the invention (T(bottom)=175° C.; T(head)=100° C.; 0.6 mbar) are obtained. A yield of 70%, based on the ketone reacted, is calculated.

Composition of the resulting nitriles according to the gas chromatogram (column: 60M DB1; temperature condition: 80-4-250° C; that is to say: gas chromatogram temperature-programmed, initial temperature: 80° C., no isothermal first runnings; heating-up rate: 4° C. per minute; final temperature: 250° C.).

Figure 2:
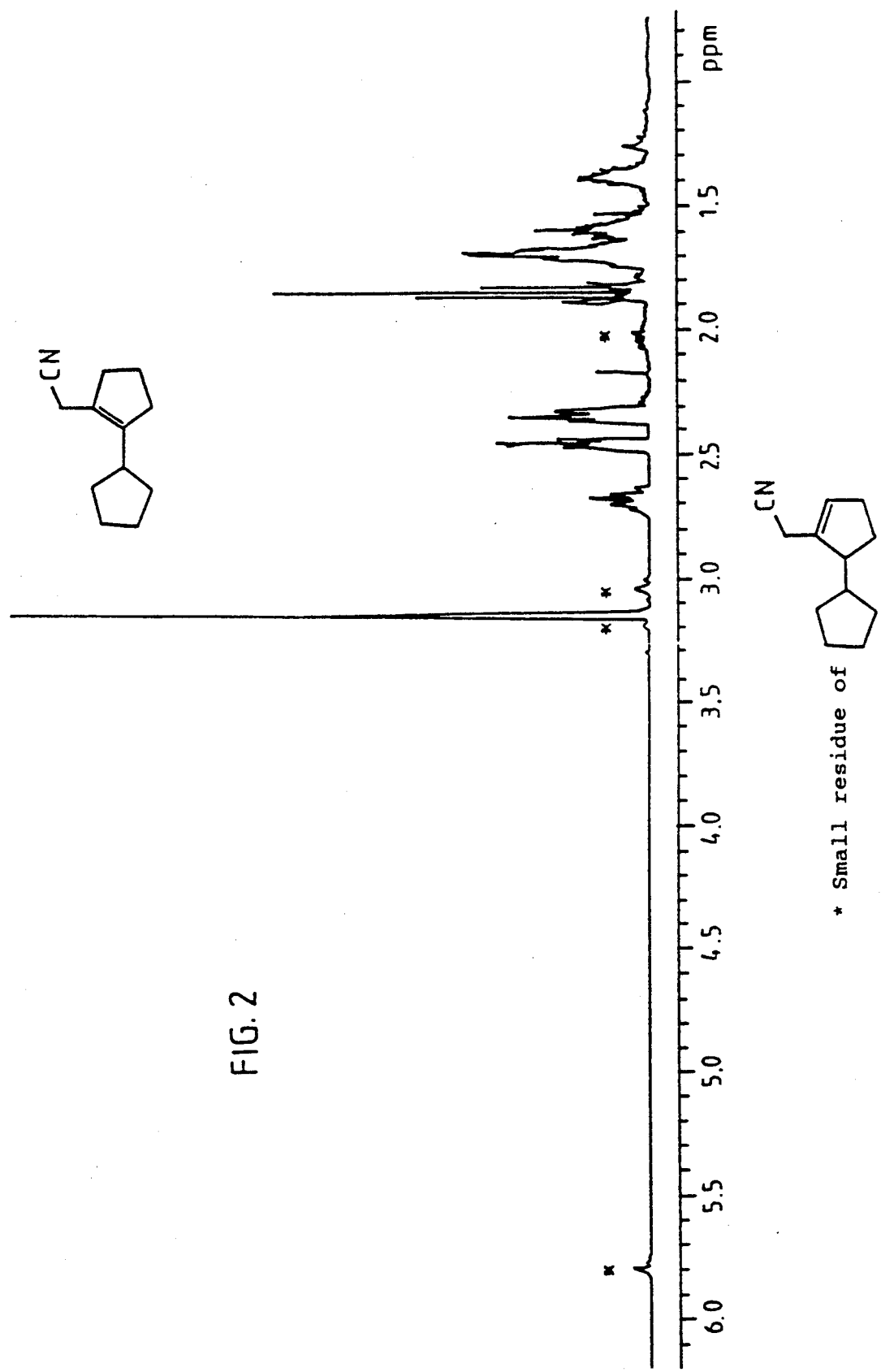

73.5% of 1-cyanomethyl-5-cyclopentyl-cyclopent-1-ene; see NMR spectrum, FIG. 1.
21.2% of 1-cyanomethyl-2-cyclopentyl-cyclopent-1-ene; see NMR spectrum, FIG. 2.
3.7% of 2-cyanomethylene-dicyclopentyl.

Example 2

382 g (4.5 mol) of cyanoacetic acid, 456 g (3.0 mol) of 2-cyclopentylcyclopentanone, 23 g of ammonium acetate (0.3 mol) and 72 g (1.2 mol) of acetic acid in 900 ml of xylene are heated under reflux, using a water separator, in the apparatus described in Example 1. After 12 hours, 101 l of $CO_2$ and 74 g of an aqueous phase have been split off. The reaction mixture is washed successively with 200 ml of 10% strength sulphuric acid, with 400 ml of 5% strength sodium hydroxide solution and with water and is distilled over a 30 cm packed column. In addition to 158 g of 2-cyclopentylcyclopentanone (T(bottom)=130° C.; (T(head)=85° C.; 0.6 mbar), 205 g of the nitriles of the formula (I) according to the invention (T(bottom)=175° C.; T(head)=100° C.; 0.6 mbar) are obtained. A yield of 60%, based on the ketone reacted, is calculated.

Composition of the resulting nitriles according to gas chromatogram (column: 60 DB 1; temperature condition: 80-4-250° C.):

34.1% of 1-cyanomethyl-5-cyclopentyl-cyclopent-1-ene;
62.9% of 1-cyanomethyl-2-cyclopentyl-cyclopent-1-ene;
3.0% of 2-cyanomethylene-dicyclopentyl.

Example 3

0.5 g (0.021 mol) of sodium is dissolved in 100 g of anhydrous isopropanol, while heating, in a three-necked flask fitted with a dropping funnel, reflux condenser and nitrogen inlet. The homogenous solution is cooled to room temperature. 100 g (0.57 mol) of a mixture of the nitriles of the formula (I) according to the invention (containing 62.8% of 1-cyanomethyl-5-cyclopentyl-cyclopent-1-ene; 34.0% of 1-cyanomethyl-2-cyclopentyl-cyclopent-1-ene; and 3.2% of 2-cyanomethylene-dicyclopentyl) are added and the mixture is subsequently stirred at room temperature for 4 hours. It is then neutralised to pH=6 with glacial acetic acid and distilled.

85.0 g of distillate of the nitriles of the formula (I) are obtained; for the composition, see below. A yield of 85%, based on the nitrile mixture employed, is calculated. The amount of residue is 13 g.

Composition of the distillate according to gas chromatogram (column: 60 m DB 1; temperature condition: 80-4-250° C.):

8.8% of 1-cyanomethyl-5-cyclopentyl-cyclopent-1-ene;
66.0% of 1-cyanomethyl-2-cyclopentyl-cyclopent-1-ene;
25.2% of 2-cyanomethylene-dicyclopentyl.

The trivial names used in the following use examples have the following meaning:

Iraldein gamma pure

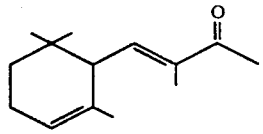

3-Methyl-4-(2,6,6-trimethylcyclohex-2-en-1-yl)-but-3-ene-2-one

Eugenol

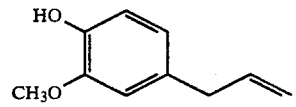

2-Methoxy-4-allylphenol

Musk ketone

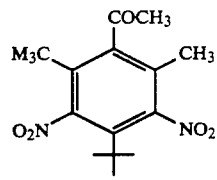

2,6-Dimethyl-3,5-dinitro-4-tert.-butylacetophenone

Vertocitral: Mixture of

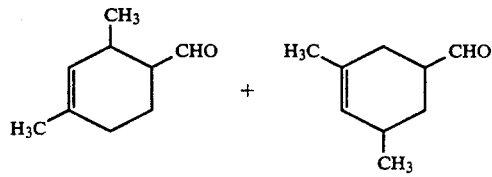

2,4-dimethyl-cyclohex-3-ene-1-aldehyde 3,5-dimethyl-cyclohex-3-ene-1-aldehyde

Evernyl

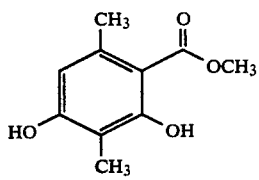

Methyl 2,5-dimethyl-4,6-dihydroxy-benzoate

Use 1

A perfume composition is prepared by mixing the following constituents (amounts stated in grams):

| | |
|---|---|
| Aldehyde C10 (decanal) | 5.0 |
| Nitriles of the formula (I), 1% strength in dipropylene glycol (0.04% strength in perfume oil) | 40.0 |
| Galbanum resin | 20.0 |
| Dist. bergamot oil | 60.0 |
| Dihydromyrcenol | 50.0 |
| Dihydromyrcenyl acetate | 40.0 |
| Citrylal (H + R) | 20.0 |
| French petit grain oil | 40.0 |
| Muguet lily of the valley base # 10689F (H + R) | 60.0 |
| Pure phenylethyl alcohol | 60.0 |
| Citronellol supra | 50.0 |
| Benzyl acetate | 50.0 |
| Alpha-hexylcinnamaldehyde | 60.0 |
| cis-3-hexenyl salicylate | 100.0 |
| Benzyl salicylate | 80.0 |
| Iraldein gamma pure | 80.0 |
| Eugenol | 10.0 |
| Mousse C abs. verte jug. 50% in TEC | 10.0 |
| Musk ketone | 80.0 |
| Dipropylene glycol | 85.0 |
| | 1,000.0 |

TEC = Triethyl citrate

The nitriles of the formula (I) employed are distinguished by the fact that even when a very small amount is added to a suitable perfume oil, the latter is caused to vary impressively in the direction of "marine freshness".

Use 2

A performed composition is prepared by mixing the following constituents (amounts stated in grams):

| | |
|---|---|
| 2-Methyldodecanal | 1.0 |
| Nitriles of the formula (I), 1% strength in dipropylene glycol (0.02% strength in perfume oil) | 2.0 |
| Vertocitral (H + R) | 0.5 |
| Dihydromyrcenol | 5.0 |
| Terpinyl acetate | 30.0 |
| Citrylal (H + R) | 4.0 |

| -continued | |
|---|---|
| Brazilian orange oil | 6.0 |
| Spanish lavender oil | 6.0 |
| Eucalyptus globulus oil, 80/85% pure | 3.0 |
| Moroccan armoise oil | 1.0 |
| Isobornyl acetate | 3.0 |
| Pure phenylethyl alcohol | 3.0 |
| Geraniol | 6.0 |
| Benzyl acetate | 4.0 |
| Alpha-hexylcinnamaldehyde | 3.0 |
| Decolorised clove leaf oil | 1.0 |
| Coumarin | 3.0 |
| Florida cedar wood oil | 6.0 |
| Evernyl (RBD) | 0.5 |
| Mousse A concr. 50% in TEC | 1.0 |
| Musk ketone | 2.0 |
| 10% strength indole in dipropylene glycol | 1.0 |
| Dipropylene glycol | 8.0 |
| | 100.0 |

The top note is given a clean freshness by addition of the nitriles of the formula (I) employed. The nitriles of the formula (I) have a very potent, fresh marine fragrance which, in dilution is reminiscent of algae, fresh fish and the coast. Herbal spicy notes of oak moss, dill and cumin are also evident.

We claim:
1. 1-Cyanomethyl-5-cyclopentyl-cyclopent-1-ene of the formula

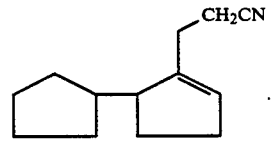

2. 1-Cyanomethyl-2-cyclopentyl-cyclopent-1-ene of the formula

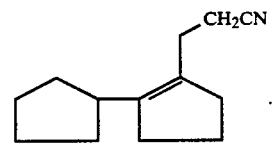

3. A performed composition comprising a substance and a perfuming amount of a compound according to claim 1.

4. A perfumed composition comprising a substance and a perfuming amount of a compound according to claim 2.

5. A method of enhancing the fragrance of a substance which comprises adding thereto an olfactorily effective amount of a compound according to claim 1.

6. A method of enhancing the fragrance of a substance which comprises adding thereto an olfactorily effective amount of a compound according to claim 2.

* * * * *

UNITED STATES PATENT AND TRADEMARK OFFICE
CERTIFICATE OF CORRECTION

PATENT NO. : 5,212,153

DATED : May 18, 1993

INVENTOR(S) : Hopp, et al.

It is certified that error appears in the above-identified patent and that said Letters Patent is hereby corrected as shown below:

Col. 6, line 45    Delete " performed " and substitute -- perfumed --

Signed and Sealed this

Thirtieth Day of August, 1994

Attest:

BRUCE LEHMAN

Attesting Officer     Commissioner of Patents and Trademarks